United States Patent [19]
Mehta et al.

[11] Patent Number: 5,648,347
[45] Date of Patent: Jul. 15, 1997

[54] ARYLMORPHOLINE, PREPARATION AND USE

[75] Inventors: Nariman Bomanshaw Mehta, Lady Lake, Fla.; Grady Evan Boswell, Cary; James Leroy Kelley, Raleigh, both of N.C.

[73] Assignee: Glaxo Wellcome Inc., Research Triangle Park, N.C.

[21] Appl. No.: 444,609

[22] Filed: May 19, 1995

Related U.S. Application Data

[63] Continuation of Ser. No. 140,010, filed as PCT/GB92/00733, Apr. 22, 1992 published as WO92/18489, Oct. 29, 1992, abandoned.

[30] Foreign Application Priority Data

Apr. 23, 1991 [GB] United Kingdom ............... 4108629

[51] Int. Cl.$^6$ ............... A61K 31/535; C07D 265/30
[52] U.S. Cl. ............... 514/231.2; 544/106; 544/107; 544/178
[58] Field of Search ............... 544/106, 178; 514/231.2

[56] References Cited

U.S. PATENT DOCUMENTS

| | | | |
|---|---|---|---|
| 2,997,469 | 8/1961 | Heel et al. | 544/106 |
| 3,117,967 | 1/1964 | Anderson et al. | 544/173 |
| 4,360,519 | 11/1982 | White et al. | |
| 4,576,944 | 3/1986 | Lafon | 514/230.8 |
| 4,714,699 | 12/1987 | Lafon | |
| 4,803,200 | 2/1989 | Munson, Jr. et al. | 514/231.2 |
| 5,104,870 | 4/1992 | Kelley et al. | 514/230.8 |

FOREIGN PATENT DOCUMENTS

| | | |
|---|---|---|
| 1 189 861 | 2/1985 | Canada. |
| 027 695 | 4/1981 | European Pat. Off.. |
| 0 139590 | 5/1985 | European Pat. Off.. |
| 0 170430 | 2/1986 | European Pat. Off.. |
| 2553411 | 10/1983 | France. |
| 851311 | 10/1960 | United Kingdom. |
| 1336732 | 10/1970 | United Kingdom. |
| 2 061 272 | 5/1981 | United Kingdom. |

OTHER PUBLICATIONS

Rekka et al., "Synthesis, Physicochemical Properties and Biological Studies of Some Substituted 2-alkoxy-4-methy-morpholines", Eur. J. Med. Chem, 24, 179–185 (1989).

Tyle, "Iontophoretic Devices for Drug Delivery", Pharmaceutical Research, 3(6), 318 (1986).

Lutz et al., "1,2–Diphenyl Amino Ketones and Alcohols. Condensation of Amines With Unsymmetrically Substituted Benzoins and Related Reactions", J. Org. Chem, 21, 49 (1956).

Lutz et al., "Substituted–Amino Ketones and Alcohols Related to 4,4'–Dichlorobenzoin", J. Am. Chem, Soc., 71, 478 (1949).

Lutz et al., "Secondary and Tertiary Amino Ketones and Alcohols Derived from Desoxybenzoin and 1,2–Diphenylethanol. Ring–chain Tautomerism of α–(β–Hydroxyethylamino) Ketones", J. Am., Chem, Soc., 70, 2015 (1948).

European Search Report EP90311851.1, 11 Dec. 1990.

*Primary Examiner*—Shean C. Wu
*Attorney, Agent, or Firm*—Robert H. Brink; Shah R. Makujima

[57] ABSTRACT

A method for the treatment of depression in a human being, the method comprising administering to the human being an antidepressant effective amount of a compound of the following formula

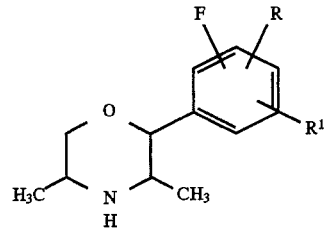

or a pharmaceutically acceptable salt thereof,
wherein R and $R^1$ are independently hydrogen or fluorine.

8 Claims, No Drawings

ARYLMORPHOLINE, PREPARATION AND USE

This is a continuation of application Ser. No. 08/140,010, filed as PCT/GB92/00733, Apr. 22, 1992, published as WO92/18489, Oct. 29, 1992, now abandoned.

The present invention relates to novel morpholines useful in medicine, to processes for preparing them, to pharmaceutical formulations containing them and their preparation, to the use of the compounds in medicine and to novel chemical intermediates therefor and the preparation thereof.

It has been found that novel morpholine compounds represented by formula (I)

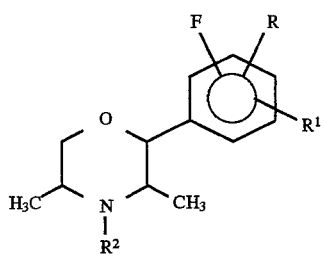

wherein R and $R^1$ are each either hydrogen or fluorine and $R^2$ is hydrogen or methyl, and salts thereof, have antidepressant activity as demonstrated by widely accepted techniques used in the art of pharmacology for determining antidepressant activity, for example, the tetrabenazine-induced sedation test in rodents. Advantageously these compounds do not produce any significant degree of locomotor stimulation and are essentially free of proconvulsant activity in the therapeutic dose range.

Structural formula (I) should be understood to extend to and embrace all geometric and optical isomers.

Preferred compounds within formula (I) are:
(+−)-(2R*,3R*,5S*)-2-(3-fluorophenyl)-3,5-dimethylmorpholine
(2S,3S,5R)-2-(3,4-difluorophenyl)-3,5-dimethylmorpholine
(+−)-(2R*,3R*,5S*)-2-(3-fluorophenyl)-3,4,5-trimethylmorpholine
(+−)-(2R*,3R*,5S*)-2-(4-fluorophenyl)-3,5-dimethylmorpholine
(2R,3R,5S)-2-(4-fluorophenyl)-3,5-dimethylmorpholine
(+−)-(2R*,3R*,5S*)-2-(2,3-difluorophenyl)-3,5-dimethylmorpholine
(2S,3S,5R)-2-(3-fluorophenyl)-3,4,5-trimethylmorpholine
(+−)-(2R*,3R*,5S*)-2-(4-fluorophenyl)-3,4,5-trimethylmorpholine and
(2S,3S,5R)-2-(4-fluorophenyl)-3,5-dimethylmorpholine
and salts thereof, in particular pharmaceutically acceptable salts, the first two of which (together with their salts) being particularly preferred.

The compounds of formula (I) and their salts may be synthesized by the methods known in the art for the preparation of compounds of analogous structure and in this regard reference is made, by way of illustration only, to the following standard texts:
i) "Protective Groups in Organic Chemistry" ed. J. F. W. McOmie, Plenum Press (1973), ISBN 0-306-30717-0;
ii) "Compendium of Organic Synthetic Methods" ed. I. T. Harrison and S. Harrison, Wiley-Interscience, Vol. I (1971) ISBN 0-471-35550-X, Vol. II (1974) ISBN 0-471-35551-8 and Vol. III (ed. L. S. Hegedus and L. Wade) (1977) ISBN 0-471-36752-4; and
iii) Rodd's "Chemistry of Carbon Compounds" second edition, Elsevier Publishing Company.

Thus the compounds of formula (I) can be prepared by cyclization of the corresponding compound of formula (II) wherein R, $R^1$ and $R^2$ are as defined for formula (I) by treatment with a dehydrating agent such as sulfuric acid in a solvent such as dichloromethane at 0° C. or by reaction with p-toluenesulfonic acid as a melt at 110°–160° C.

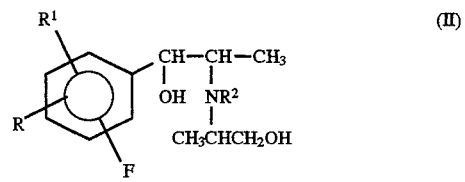

The compounds of formula (I) wherein $R^2$ is methyl may also be prepared by methylation of the corresponding compound of formula (I) wherein $R^2$ is hydrogen using for example aqueous formaldehyde and formic acid at 50°–100° C.; methyl iodide in acetonitrile at 50°–100° C.; formylation followed by reduction; and reaction with diazomethane in the presence of a Lewis acid such as borontrifluoride etherate.

Compounds of formula (II) can be prepared by selective reduction of the corresponding morpholinol of formula (III) wherein R, $R^1$ and $R^2$ are as defined for formula (I) using a mild reducing agent such as sodium borohydride in 95% ethanol or diborane in tetrahydrofuran, or any other appropriate reducing agent.

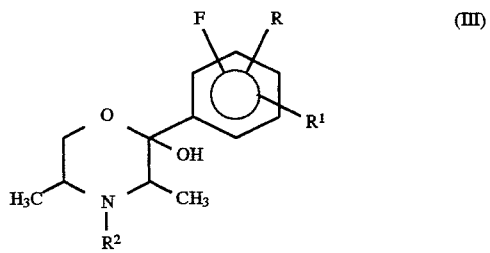

The morpholinols of formula (III) can be made by reacting a compound (IV) having the appropriate chirality with a compound of formula (V) wherein R, $R^1$ and $R^2$ are as defined for formula (I) and L is a leaving atom or group such as halo (for example, bromo, chloro or iodo) in a suitable solvent such as acetonitrile, ethanol, methanol or dichloromethane in the presence of a base, for example, 2,6-lutidine. The reaction may conveniently be performed at a temperature in the range of 20° to 40° C.

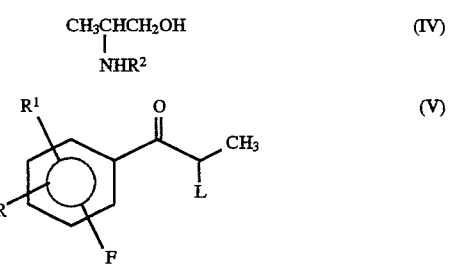

It will be appreciated that use in this manner of a racemic compound (IV), i.e. a dl-2-amino-1-propanol, affords the (+−)-(2R*,3R*,5S*) racemate of formula (III) while an R-2-amino-1-propanol selectively provides the (2S,3S,5R) compound and an S-2-amino-1-propanol selectively provides the (2R,3R,5S) compound.

It will further be understood that a (+−)-(2R*,3R*,5S*) racemate of formula (III) will ultimately provide, in the manner above described, the (+−)-(2R*,3R*,5S*) racemate of formula (I), whilst the (2S,3S,5R) and (2R,3R,5S) compounds (III) will likewise afford the (2S,3S,5R) and (2R,3R,5S) compounds (I) respectively.

The (2S,3S,5R) compounds and (2R,3R,5S) compounds of formulae (I) and (III) can also be selectively obtained by resolution of the appropriate (+−)-(2R*,3R*,5S*) racemate. This may be accomplished in a conventional manner, by forming the diastereomeric salts of the latter with an optically active acid, for example (+)- or (−)-tartaric acid or (+)- or (−)-dibenzoyl-L- or D-tartaric acid monohydrate, in an appropriate solvent, for example aqueous ethanol, followed by recrystallization of the appropriate diastereomeric salt and isolation of the morpholine/morpholinol free base.

The compounds of formula (I) and their pharmaceutically acceptable salts may be used in the treatment of depression in human beings, identified as being depressed, the treatment comprising the administration of an antidepressant effective, non-toxic amount (dose), preferably in a unit dosage form, of a compound of formula (I) or a pharmaceutically acceptable salt thereof.

Depression states in the treatment of which the said compounds and salts are particularly useful are those classified as affective disorders in the *Diagnostic and Statistical Manual of Mental Disorders,* Third Edition—Revised, American Psychiatric Association, Washington, D.C. (1987) (DSM-III-R), including the mood disorders (DSM-III-R, 296.2X to 296.6X), other specific affective disorders (301.13 and 300.40) and bipolar and depressive disorders not otherwise specified (296.70 and 311.00).

Other uses in human therapy for these compounds and salts include the treatment of the following conditions, the classifications (where indicated) being those adopted in DSM-III-R:

- anxiety disorders, including phobic neuroses (300.00, 300.21, 300.22, 300.23 and 300.29), anxiety neuroses (300.01, 300.02 and 300.30) and post-traumatic stress disorder (309.89)
- attention deficit disorders (314.00 and 314.01)
- eating disorders, including anorexia nervosa (307.10) and bulimia (307.51)
- personality disorders, including borderline personality disorder (301.83)
- sexual dysfunctions, including hypoactive sexual desire disorder (302.71), female sexual arousal disorder or male erectile disorder (302.72), inhibited female orgasm (302.73), inhibited male orgasm (302.74), premature ejaculation (302.75), dyspareunia (302.76), vaginismus (306.51) and sexual dysfunction not otherwise specified (302.70)
- headaches, including migraine, muscle contraction and mixed (i.e. combination of migraine and muscle contraction) headaches
- narcolepsy-cataplexy syndrome, a condition characterized by excessive sleepiness (narcolepsy) often taking the form of sleep attacks, episodes of a seemingly irresistible need to sleep usually lasting for about fifteen minutes or less, together with brief (often lasting less than a minute) periods of loss of muscle tone (cataplexy) occurring in association with the expression of emotion.

The compounds and salts may further be used in human medicine:

- to alleviate symptoms of withdrawal consequent upon the cessation of illicit drug abuse
- to potentiate the analgesia induced by morphine or a like opiate analgesic, for example in the care and treatment of terminally-ill cancer patients
- to prevent functional impairment and drowsiness following administration of a drowsiness-inducing benzodiazepine tranquilizer; suitable indications for concomitant administration of a said compound or salt and such a benzodiazepine include a) treatment of mixed anxiety and depression in situations where functional impairment or drowsiness is undesirable, and b) treatment of anxiety in situations where functional impairment or drowsiness is undesirable
- to prevent memory loss following administration of a benzodiazepine tranquilizer
- to restore mental functioning acutely impaired consequent upon ethanol ingestion
- to suppress prolactin release or secretion, for example in the suppression of lactation postpartum or in the treatment of galactorrhoea, hyperprolactinaemia, amenorrhoea resulting from hyperprolactinaemia and prolactin-sensitive mammary cancer
- to treat memory loss and other memory deficits associated with benign senility.

For each of the foregoing indications, the preferred dosage for parenteral (including subcutaneous, intramuscular and intravenous) administration of a compound of formula (I) or salt thereof (estimated as the base) is in the range 0.05 mg/kg to 10 mg/kg of body weight per day. The most preferred dosage is in the range of 0.25 mg/kg to 5 mg/kg of body weight per day.

For the oral, rectal, topical (including buccal and sublingual) or transdermal mode of administration, the preferred dosage of a compound of formula (I) or salt thereof (estimated as the base) is in the range 0.25 mg/kg to 20 mg/kg of body weight per day while the most preferred dosage is in the range of 0.5 mg/kg to 10 mg/kg of body weight per day.

As will be understood, the precise dosage will depend upon a number of clinical factors, for example, the age of the recipient and the condition in question and its severity.

The preferred unit dosage of a compound of formula (I) or salt thereof (estimated as the base) for oral, rectal or topical (including buccal and sublingual) administration is in the range 2.5 mg to 200 mg with the more preferred unit dosage being in the range 5 mg to 150 mg and the most preferred unit dosage being in the range 10 mg to 100 mg. For parenteral (including subcutaneous, intramuscular and intravenous) administration, the preferred unit dosage is in the range 1 mg to 125 mg with the more preferred unit dosage being in the range 2.5 mg to 100 mg and the most preferred unit dosage being in the range 5 mg to 50 mg.

All the above doses are expressed in terms of the weight of the base but a compound of formula (I) is preferably administered in the form of a pharmaceutically acceptable salt thereof.

A compound of formula (I) or salt thereof is preferably administered four times daily although this may vary according to the patient being treated, and at the physician's discretion.

While it is possible for the active compound, i.e., compound of formula (I) or pharmaceutically acceptable salt thereof, to be administered alone as the raw chemical, it is preferable to present it as a pharmaceutical formulation comprising a compound of formula (I) (or a pharmaceutically acceptable salt thereof) together with an acceptable carrier therefor.

The carrier should be acceptable in the sense of being compatible with the other ingredients of the formulation and not deleterious to the recipient thereof.

Conveniently the active compound comprises from 5 to 95% by weight of the formulation.

The formulations include those suitable for oral, rectal, topical (including buccal and sublingual), parenteral (including subcutaneous, intramuscular and intravenous) or transdermal administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier or both and then, if necessary, snaping the product.

Formulations of the present invention suitable for oral administration may be presented as discrete units such as capsules, cachets, tablets or lozenges, each containing a predetermined amount of the active compound; as a powder or granules including microencapsulated or time-release forms; or as a suspension or solution in an aqueous liquid or non-aqueous liquid such as a syrup, an elixir, an emulsion or a draught.

A tablet may be made by compression or molding, optionally with one or more accessory ingredients. Compressed tablets may be prepared by compressing in a suitable machine, the active compound being in a free-flowing form such as a powder or granules optionally mixed with a binder, disintegrant, lubricant, inert diluent, surface active agent or dispersing agent. Molded tablets comprising a mixture of the powdered active compound with any suitable carrier may be made by molding in a suitable machine.

Formulations suitable for rectal administration may be presented as a suppository with a conventional carrier such as cocoa butter, hydrogenated fats or hydrogenated fatty carboxylic acids.

Formulations suitable for topical administration in the mouth, for example buccally or sublingually, include lozenges comprising the active compound in a flavored basis such as sucrose and acacia or tragacanth, and pastilles comprising the active compound in a basis such as gelatin and glycerin or sucrose and acacia.

Formulations suitable for parenteral administration conveniently comprise a sterile aqueous preparation of the active compound which is preferably isotonic with the blood of the intended recipient. The formulations may be presented in unit-dose or multi-dose containers, for example sealed ampules and vials, and may be stored in a freeze-dried state requiring only the addition of the sterile liquid carrier, for example water, just prior to use. As an alternative possibility, the active compound may be presented in the form of liposomes.

Formulations suitable for transdermal administration may be presented as discrete patches adapted to remain in intimate contact with the epidermis of the recipient for a prolonged period of time. Such patches suitably contain the active compound 1) in an optionally buffered, aqueous solution, 2) dissolved and/or dispersed in an adhesive or 3) dispersed in a polymer, a suitable concentration of the active compound being in the range of about 1% to 35%, preferably about 3% to 15% (w/w). As one particular possibility, the active compound may be delivered from the patch by electrotransport or iontophoresis as generally described in Pharmaceutical Research, 3(6), 318 (1986).

In addition to the aforementioned ingredients, the formulations of this invention may further include one or more accessory ingredient(s) selected as appropriate from diluents, buffers, flavoring agents, binders, disintegrants, surface active agents, thickeners, lubricants, preservatives (including antioxidants) and the like.

When used in medicine, the salts of a compound of formula (I) should be pharmaceutically acceptable, but pharmaceutically unacceptable salts may conveniently be used to prepare the corresponding free base or pharmaceutically acceptable salts thereof and are included within the scope of this invention.

Such pharmaceutically acceptable salts include, but are not limited to, those prepared from the following acids: hydrochloric, hydrobromic, sulfuric, nitric, phosphoric, salicylic, p-toluenesulfonic, tartaric, citric, methanesulfonic, maleic, formic, malonic, succinic, isethionic, lactobionic, napththalene-2-sulfonic, sulfamic, ethanesulfonic and benzenesulfonic.

Published patent specification U.S. Pat. No. 4,803,200 discloses a large class of dialkanolamines, thiol analogues and 1,4-oxazine condensation derivatives thereof, embracing the morpholine compounds of formula (I) herein, and teaches their use in combatting viral infections in animals, especially mammals such as cattle, sheep, goats, horses, buffalo, deer and the like, particularly those viral infections associated with shipping fever.

The said US-A specification further states that certain of the subject compounds were prepared and reported to be antitumour agents in the following disclosures:

R. E. Lutz and R. S. Murphey in *J. Am. Chem. Soc.* 71, 478 (1949),

R. E. Lutz and J. W. Baker in *J. Org. Chem.* 21, 49 (1956), and

R. E. Lutz, J. A. Freek and R. S. Murphey in *J. Am Chem. Soc.* 70, 2015 (1948).

None of the compounds specifically identified in either the US-A specification itself or the said disclosures falls within formula (I) herein.

It will be appreciated from the foregoing that in various aspects the present invention provides the following, inter alia:

a) compounds of formula (I) as hereinbefore defined and salts thereof together with methods for their preparation as hereinbefore described b) pharmaceutical formulations as hereinbefore defined together with methods for their preparation as hereinbefore described c) compounds of formula (I) and pharmaceutically acceptable salts thereof for use in human or veterinary medicine, in particular in the treatment of depression in human beings d) use of compounds of formula (I) and pharmaceutically acceptable salts thereof for the manufacture of medicaments for the treatment of depression in human beings.

e) a method for the treatment of depression in human beings comprising administration of a compound of formula (I) or a pharmaceutically acceptable salt thereof.

f) novel chemical intermediates together with methods for their preparation as hereinbefore described.

The following Examples are provided by way of illustration of the present invention and should in no way be construed as a limitation thereof.

EXAMPLE 1

(+−)-(2R*,3R*,5S*)-2-(3-fluorophenyl)-3,5-dimethylmorpholine hydrochloride

To a solution of 3'-fluoropropiophenone (Aldrich Chemical Co., Milwaukee, Wis. 53233) (61 g, 0.4 mole) in dioxane (300 ml) was added a solution of dioxane dibromide (99 g, 0.4 mole) in dioxane (200 ml). [The dioxane dibromide solution was prepared by the addition of bromine (64 g, 0.4 mole) to dioxane (200 ml)]. The reaction mixture was stirred for one hour at room temperature, diluted with water and extracted with dichloromethane. The organic layers were combined, washed with brine, dried (potassium carbonate), and concentrated under reduced pressure to yield crude 2-bromo-3'-fluoropropiophenone (103 g).

To a solution of 2-bromo-3'-fluoropropiophenone (46.2 g, 0.2 mole) in acetonitrile (150 ml) was added a solution of dl-2-amino-1-propanol (Aldrich Chemical Co., Milwaukee, Wis. 53233) (16.5 g, 0.22 mole) and 2,6-lutidine (23.6 g, 0.22 mole) in acetonitrile (100 ml). The resulting mixture was stirred for 72 hours at room temperature.

The reaction was filtered, the solid was washed with a small amount of acetonitrile followed by dry diethyl ether and dried to give 29.6 g of (+−)-(2R*,3R*,5S*)-3,5-dimethyl-2-(3-fluorophenyl)-2-morpholinol hydrobromide.

To a solution of (+−)-(2R*,3R*,5S*)-3,5-dimethyl-2-(3-fluorophenyl)-2-morpholinol hydrobromide (29.6 g, 0.097 mole) in 50—50 ethanol-water (200 ml) was added a solution of sodium borohydride (14.6 g, 0.387 mole) in water (200 ml) at 0° C. The resulting mixture was stirred for 16 hours at room temperature, treated with concentrated hydrochloric acid and concentrated under reduced pressure. The residue was dissolved in water, basified (50% aqueous sodium hydroxide), and extracted with dichloromethane. The organic layers were combined, washed with brine, dried (potassium carbonate), and concentrated under reduced pressure to give 23.6 g of (1R*,2S*)-2-[[(1RS-2-hydroxy-1-methylethyl]amino]-1-(3-fluorophenyl)propanol as a white solid.

To concentrated $H_2SO_4$ (75 ml) was added a solution of (1R*,2S*)-2-[[(1RS)-2-hydroxy-1-methylethyl]amino]-1-(3-fluorophenyl)propanol (21.6 g, 0.095 mole) in dichloromethane (100 ml) at 0° C. The resulting mixture was stirred for 16 hours at room temperature and diluted with ice water. The aqueous phase was basified with 40% aqueous sodium hydroxide and extracted with diethyl ether. The diethyl ether layers were combined, washed with brine, dried (sodium sulfate), and concentrated under reduced pressure to yield the crude reaction product as the free base. The crude product was dissolved in diethyl ether and treated with ethereal hydrogen chloride. Recrystallization from ethanol-diethyl ether mixtures gave 17.7 g of (+−)-(2R*,3R*,5S*)-2-(3-fluorophenyl)-3,5-dimethylmorpholine hydrochloride as a white solid, m.p. 268°–269° C.

NMR-$^1$H: (DMSO-$d_6$) δ 0.98 (d, 3H, $CH_3$), 1.22 (d, 3H, $CH_3$), 3.42 (broad multiplet, 2H, CH), 3.62 (dd, 1H, $CH_2$, J=11.09, 11.61), 4.02 (dd, 1H, $CH_2$, J=3.12, 11.91), 4.44 (d, 1H, CH, J=9.92), 7.15–7.49 (aromatic H's), 9.46 and 10.00 (broad, 2H, HCl and NH).

Elemental Analysis: Calcd. for $C_{12}H_{17}ClFNO$ (m.w. 245.724): C, 58.65%; H, 6.97%; N, 5.70%, Found: C, 58.72%; H, 7.01%; N, 5.68%.

EXAMPLE 2

(2S,3S,5R)-2-(3,4-difluorophenyl)-3,5-dimethylmorpholine hydrochloride

To 3',4'-difluoropropiophenone (Alfa Products, Danvers, Mass. 01923) (90.5 g, 0.53 mole) was added a solution of dioxane dibromide (131 4 g, 0.53 mole) in dioxane (500 ml). The reaction was worked up as in Example 1 to yield crude 2-bromo-3',4'-difluoropropiophenone (130.5 g).

To a solution of 2-bromo-3',4'-difluoropropiophenone (47.3 g, 0.19 mole) in acetronitrile (100 ml) was added a solution of R-2-amino-1-propanol (Aldrich Chemical Co., Milwaukee, Wis. 53233) (15 g, 0.20 mole) and 2,6-lutidine (23.6 g, 0.22 mole) in acetonitrile (50 ml). The reaction was worked up as in Example 1 to give 26.9 g of (2S,3S,5R)-2-(3,4-difluorophenyl)-3,5-dimethyl-2-morpholinol hydrobromide.

A solution of (2S,3S,5R)-2-(3,4-difluorophenyl)-3,5-dimethyl-2-morpholinol hydrobromide (4.85 g, 0.015 mole) in water was basified with 40% aqueous sodium hydroxide and extracted with diethyl ether. The diethyl ether layers were combined, washed with brine, dried (potassium carbonate) and concentrated under reduced pressure to yield the free base. The free base was dissolved in ether and treated with ethereal hydrogen chloride. The hydrochloride salt was recrystallized from ethanol-diethyl ether mixtures to give 3.26 g of (2S,3S,5R)-2-(3,4-difluorophenyl)-3,5-dimethyl-2-morpholinol hydrochloride as a white solid. m.p. 223°–225° C. dec.

Elemental Analysis: Calcd. for $C_{12}H_{16}ClF_2NO_2$ (m.w. 279.71): C, 51.52%, H, 5.77%; N, 5.01%. Found: C, 51.54%; H, 5.80%; N, 4.98%. $[\alpha]_D^{20}$=+42.16° (c=0.676, abs. ethanol).

To a solution of (2S,3S,5R)-2-(3,4-difluorophenyl)-3,5-dimethyl-2-morpholinol hydrobromide (25.4 g, 0.078 mole) in 50—50 ethanol-water (300 ml) was added a solution of sodium borohydride (11.9 g, 0.31 mole) in water (120 ml) at 0° C. The resulting mixture was stirred for 16 hours at room temperature. The reaction mixture was treated with concentrated hydrochloric acid and concentrated under reduced pressure. The residue was dissolved in water, basified (40% aqueous sodium hydroxide), and extracted with dichloromethane. The organic layers were combined, washed with brine and dried (potassium carbonate) to give a solution of (1R,2S)-1-(3,4-difluorophenyl)-2-[[(1R)-2-hydroxy-1-methylethyl]amino]propanol in dichlomethane (500 ml). 50 ml of the solution was concentrated under reduced pressure to yield 1.9 g of the free base as a white solid. The free base was dissolved in diethyl ether and treated with ethereal hydrogen chloride. The hydrochloride salt was recrystallized from ethanol-diethyl ether mixtures to give 1.1 g of (1R,2S)-1-(3,4-difluorophenyl)-2-[[(1R)-2-hydroxy-1-methylethyl]amino]propanol hydrochloride as a white solid. m.p. 116°–117° C.

Elemental Analysis: Calcd. for $C_{12}H_{18}ClF_2NO_2$ (m.w. 281.73): C, 51.16%; H, 6.44%; N, 4.97%. Found: C, 51.06%; H, 6.48%; N, 4.95%. $[\alpha]_D^{20}$=−29.0° (95% ethanol).

To concentrated $H_2SO_4$ (100 ml) was added a solution of (1R,2S)-1-(3,4-difluorophenyl)-2-[[(1R)-2-hydroxy-1-methylethyl]amino]propanol (17.1 g, 0.07 mole) in dichloromethane (100 ml). The reaction was worked up as in Example 1 to yield the crude reaction product as the free base. The crude product was dissolved in diethyl ether and treated with ethereal hydrogen chloride. The hydrochloride salt was recrystallized from ethanol-diethyl ether mixtures to give 9.2 g (49.8% of theory) of (2S,3S,5R)-2-(3,4-difluorophenyl)-3,5-dimethylmorpholine hydrochloride as a white solid. m.p. 318° C. $[\alpha]_D^{20}$=+24.6° (c=0.710, 95% ethanol).

NMR-$^1$H: (DMSO-$d_6$) δ 0.96 (d, 3H, $CH_3$), 1.20 (d, 3H, $CH_3$), 3.42 (broad multiplet, 2H, CH), 3.59 (dd, 1H, $CH_2$, J=10.94, 11.67), 4.01 (dd, 1H, $CH_2$, J=2.97, 11.72), 4.40 (d, CH, J=9.81), 7.21–7.58 (aromatic H's), 9.36 and 9.95 (broad, 2H, HCl and NH).

Elemental Analysis: Calcd. for $C_{12}H_{16}ClF_2NO$ (m.w. 263.71): C, 54.65%; H, 6.12%; N, 5.31%. Found: C, 54.74%; H, 6.15%; N, 5.30%.

The following compounds of Examples 3–13 were synthesized from the appropriate starting materials using procedures analogous to those described in Example 1 and Example 2 above. In the case of the (2R,3R,5S) compounds, S-2-amino-1-propanol (Aldrich Chemical Co., Milwaukee, Wis. 53233) was employed.

EXAMPLE 3

(2S,3S,5R)-2-(3-fluorophenyl)-3,5-dimethylmorpholine hydrochloride m.p. 324°–325° C. $[\alpha]_D^{20}$=+20.9° (c=0.721, 95% ethanol).

NMR-$^1$H: (DMSO-d$_6$) δ 0.97 (d, 3H, CH$_3$), 1.21 (d, 3H, CH$_3$), 3.41 (broad multiplet, 2H, CH), 3.58 (dd, 1H, CH$_2$, J=10.94, 11.72), 4.01 (dd, 1H, CH$_2$, J=2.97, 11.87), 4.42 (d, 1H, CH, J=9.96), 7.15–7.48 (aromatic H's), 9.42 and 9.98 (broad, 2H, HCl and NH).

Elemental Analysis: Calcd. for C$_{12}$H$_{17}$ClFNO (m.w. 245.72): C, 58.66%; H, 6.97%; N, 5.70%. Found: C, 58.72%; H, 7.00%; N, 5.66%.

EXAMPLE 4

(2R,3R,5S)-2-(3-fluorophenyl)-3,5-dimethylmorpholine hydrochloride m.p. 323°–325° C. $[\alpha]_D^{20}$=−23.1° (c=0.671, 95% ethanol).

NMR-$^1$H: (DMSO-d$_6$) δ 0.98 (d, 3H, CH$_3$), 1.22 (d, 3H, CH$_3$), 3.43 (broad multiplet, 2H, CH), 3.63 (dd, 1H, CH$_2$, J=10.98, 11.72), 4.02 (dd, 1H, CH$_2$, J=3.08, 11.71), 4.44 (d, 1H, CH, J=9.81), 7.17–7.49 (aromatic H's), 9.46 and 10.01 (broad, 2H, HCl and NH).

Elemental Analysis: Calcd. for C$_{12}$H$_{17}$ClFNO (m.w. 245.72): C, 58.66%; H, 6.97%; N, 5.70%. Found: C, 58.74%; H, 7.01%; N, 5.71%.

EXAMPLE 5

(+−)-(2R*,3R*,5S*)-2-(2-fluorophenyl)-3,5-dimethylmorpholine hydrochloride m.p. 228°–230° C.

NMR-$^1$H: (DMSO-d$_6$) δ 1.01 (d, 3H, CH$_3$), 1.22 (d, 3H, CH$_3$), 3.46 (broad multiplet, 2H, CH), 3.66 (dd, 1H, CH$_2$, J=10.94, 12.15), 4.04 (dd, 1H, CH$_2$, J=3.04, 11.65), 4.78 (d, 1H, CH, J=9.96), 7.20–7.55 (aromatic H's), 9.45 and 9.95 (broad, 2H, HCl and NH).

Elemental Analysis: Calcd. for C$_{12}$H$_{17}$ClFNO (m.w. 245.72): C, 58.66%; H, 6.97%; N, 5.70%. Found: C, 58.78%; H, 7.02%; N, 5.66%.

EXAMPLE 6

(2R,3R,5S)-2-(4-fluorophenyl)-3,5-dimethylmorpholine hydrochloride m.p. 299°–300° C. $[\alpha]_D^{20.5}$=−24.9° (c=0.708, 95% ethanol).

NMR-$^1$H: (DMSO-d$_6$) δ 0.96 (d, 3H, CH$_3$), 1.22 (d, 3H, CH$_3$), 3.42 (broad multiplet, 2H, CH), 3.62 (dd, 1H, CH$_2$, J=10.94, 11.72), 4.01 (dd, 1H, CH$_2$, J=3.08, 11.72), 4.41 (d, CH, J=9.96), 7.17–7.47 (aromatic H's), 9.42 and 9.96 (broad, 2H, HCl and NH).

Elemental Analysis: Calcd. for C$_{12}$H$_{17}$ClFNO (m.w. 245.72): C, 58.66%; H, 6.97%; N, 5.70%. Found: C, 58.73%; H, 7.00%; N, 5.66%.

EXAMPLE 7

(+−)-(2R*,3R*,5S*)-2-(2,3-difluorophenyl)-3,5-dimethylmorpholine hydrochloride m.p. 285°–286° C.

NMR-$^1$H: (DMSO-d$_6$) δ 1.04 (d, 3H, CH$_3$), 1.23 (d, 3H, CH$_3$), 3.41 (broad multiplet, 2H, CH), 3.69 (dd, 1H, CH$_2$, J=11.17, 11.92), 4.04 (dd, 1H, CH$_2$, J=3.32, 11.93), 4.84 (d, 1H, CH, J=9.96), 7.21–7.53 (aromatic H's), 9.58 and 10.05 (broad, 2H, HCl and NH).

Elemental Analysis: Calcd. for C$_{12}$H$_{16}$ClF$_2$NO (m.w. 263.71): C, 54.65%; H, 6.12%; N, 5.31%. Found: C, 54.57%; H, 6.14%; N, 5.27%.

EXAMPLE 8

(+−)-(2R*,3R*,5S*)-2-(3,4-difluorophenyl)-3,5-dimethylmorpholine hydrochloride m.p. 256°–257° C.

NMR-$^1$H: (DMSO-d$_6$) δ 0.98 (d, 3H, CH$_3$), 1.21 (d, 3H, CH$_3$), 3.46 (broad multiplet, 2H, CH), 3.61 (dd, 1H, CH$_2$, J=10.94, 11.72), 4.01 (dd, 1H, CH$_2$, J=3.09, 11.72), 4.42 (d, 1H, CH, J=9.97), 7.22–7.59 (aromatic H's), 9.42 and 10.02 (broad, 2H, HCl and NH).

Elemental Analysis: Calcd. for C$_{12}$H$_{16}$ClF$_2$NO (m.w. 263.71): C, 54.65%; H, 6.12%; N, 5.31%. Found: C, 54.73%; H, 6.15%; N, 5.25%.

EXAMPLE 9

(+−)-(2R*,3R*,5S*)-2-(3,5-difluorophenyl)-3,5-dimethylmorpholine hydrochloride m.p. 331°–334° C. (sublimed).

NMR-$^1$H: (DMSO-d$_6$) δ 1.00 (d, 3H, CH$_3$), 1.22 (d, 3H, CH$_3$), 3.39 (broad multiplet, 2H, CH), 3.63 (dd, 1H, CH$_2$, J=10.94, 11.87), 4.01 (dd, 1H, CH$_2$, J=3.12, 11.76), 4.46 (d, 1H, CH, J=9.92), 7.11–7.31 (aromatic H's), 9.52 and 10.16 (broad, 2H, HCl and NH).

Elemental Analysis: Calcd. for C$_{12}$H$_{16}$ClF$_2$NO (m.w. 263.71): C, 54.65%; H, 6.12%; N, 5.31%. Found: C, 54.57%; H, 6.12%; N, 5.28%.

EXAMPLE 10

(+−)-(2R*,3R*,5S*)-3,5-dimethyl-2-(2,4,5-trifluorophenyl)morpholine hydrochloride m.p. 260°–263° C.

NMR-$^1$H: (DMSO-d$_6$) δ 1.02 (d, 3H, CH$_3$), 1.21 (d, 3H, CH$_3$), 3.47 (broad multiplet, 2H, CH), 3.65 (dd, 1H, CH$_2$, J=11.09, 11.91), 4.03 (dd, 1H, CH$_2$, J=3.32, 12.11), 4.75 (d, 1H, CH, J=9.92), 7.56–7.73 (aromatic H's), 9.45 and 10.01 (broad, 2H, HCl and NH).

Elemental Analysis: Calcd. for C$_{12}$H$_{15}$ClF$_3$NO (m.w. 281.71): C, 51.16%; H, 5.37%; N, 4.97%. Found: C, 51.26%; H, 5.40%; N, 4.98%.

EXAMPLE 11

(+−)-(2R*,3R*,5S*)-2-(2,4-difluorophenyl)-3,5-dimethylmorpholine hydrochloride m.p. 254°–256° C.

NMR-$^1$H: (DMSO-d$_6$) δ 1.01 (d, 3H, CH$_3$), 1.22 (d, 3H, CH$_3$), 3.42 (broad multiplet, 2H, CH), 3.66 (dd, 1H, CH$_2$, J=11.09, 11.91), 4.02 (dd, 1H, CH$_2$, J=3.32, 11.96), 4.76 (d, 1H, CH, J=9.96), 7.12–7.63 (aromatic H's), 9.54 and 10.05 (HCl and NH).

Elemental Analysis: Calcd. for $C_{12}H_{16}ClF_2NO$ (m.w. 263.71): C, 54.65%; H, 6.12%; N, 5.31%. Found: C, 54.60%; H, 6.15%; N, 5.32%.

EXAMPLE 12

(2S,3S,5R)-2-(4-fluorophenyl)-3,5-dimethylmorpholine hydrochloride m.p. 298°–299° C. $[\alpha]_D^{20.5}$=+25.0° (c=0.814, 95% ethanol).

NMR-$^1$H: (DMSO-$d_6$) δ 0.95 (d, 3H, $CH_3$), 1.21 (d, 3H, $CH_3$), 3.42 (broad multiplet, 2H, CH), 3.61 (dd, 1H, $CH_2$, J=10.99, 11.67), 4.01 (dd, 1H, $CH_2$, J=2.93, 11.67), 4.40 (d, 1H, CH, J=9.97), 7.17–7.47 (aromatic H's), 9.40 and 9.92 (broad, 2H, HCl and NH).

Elemental Analysis: Calcd. for $C_{12}H_{17}ClFNO$ (m.w. 245.72): C, 58.66%; H, 6.97%; N, 5.70%. Found: C, 58.72%; H, 7.01%; N, 5.67%.

EXAMPLE 13

(+−)-(2R*,3R*,5S*)-2-(4-fluorophenyl)-3,5-dimethylmorpholine hydrochloride m.p. 238°–240° C.

NMR-$^1$H: (DMSO-$d_6$) δ 0.98 (d, 3H, $CH_3$), 1.24 (d, 3H, $CH_3$), 3.41 (broad multiplet, 2H, CH), 3.68 (dd, 1H, $CH_2$, J=11.13, 11.87), 3.99 (dd, 1H, J=3.34, 12.06), 4.48 (d, 1H, CH, J=9.78), 7.16–7.46 (aromatic H's), 9.75 (broad, 1H, HCl or NH), other proton not included on spectrum.

Elemental Analysis: Calcd. for $C_{12}H_{17}ClFNO$ (m.w. 245.72): C, 58.66%; H, 6.97%; N, 5.70%. Found: C, 58.75%; H, 6.99%; N, 5.69%.

EXAMPLE 14

(+−)-(2R*,3R*,5S*)-2-(3-fluorophenyl)-3,4,5-trimethylmorpholine hydrochloride

To 95% formic acid (2.5 ml, 0.069 mole) was added (+−)-(2R*,3R*,5S*)-2-(3-fluorophenyl)-3,5-dimethylmorpholine (Example 1) (4.1 g, 0.0196 mole) and 37% aqueous formaldehyde (2.2 ml, 0.075 mole). The mixture was heated on a steam bath for 15 hours, treated with 1N hydrochloric acid and concentrated under reduced pressure. The residue was taken up in water and washed with diethyl ether, and the ether extract was discarded. The aqueous phase was basified with 40% sodium hydroxide and extracted with diethyl ether. The ether layers were combined, washed with brine, dried (potassium carbonate) and concentrated under reduced pressure to give the free base.

The free base was dissolved in ether and treated with ethereal hydrogen chloride. The hydrochloride salt was recrystallized from ethanol-diethyl ether mixtures to give 3.93 g of (+−)-(2R*,3R*,5S*)-2-(3-fluorophenyl)-3,4,5-trimethylmorpholine hydrochloride as a white solid. m.p. 188°–191° C.

NMR-$^1$H: (DMSO-$d_6$) δ 1.04 (d, 3H, $CH_3$), 1.30 (d, 3H, $CH_3$), 2.82 (d, 3H, N-Me); 3.48 (broad multiplet, 2H, CH), 3.78 (dd, 1H, $CH_2$, J=11.18, 12.26), 4.01 (dd, 1H, $CH_2$, J=3.52, 12.50), 4.56 (d, CH, J=9.96), 7.33–7.38 (aromatic H's), 11.2 (broad, 1H, HCl).

Elemental Analysis: Calcd. for $C_{13}H_{19}ClFNO$ (m.w. 259.74): C, 60.11%; H, 7.37%; N, 5.39%. Found: C, 60.21%; H, 7.42%; N, 5.37%.

The following compounds of Examples 15–21 were prepared from the appropriate starting materials, using a procedure analogous to that described in Example 14 above.

EXAMPLE 15

(+−)-(2R*,3R*,5S*)-2-(2-fluorophenyl)-3,4,5-trimethylmorpholine 4-toluenesulfonate m.p. 161°–163° C.

NMR-$^1$H: (DMSO-$d_6$) δ 1.05 (d, 3H, $CH_3$), 1.26 (d, 3H, $CH_3$), 2.28 (S, 3H, ArMe); 2.92 (S, 3H, N-Me); 3.55 (broad m, 2H, CH); 3.66 (dd, 1H, $CH_2$, J=11.13, 12.22), 4.09 (dd, 1H, $CH_2$, J=3.02, 12.38), 4.76 (d, 1H, CH, J=10.12), 7.10–7.52 (aromatic H's), 9.55 (broad, S, 1H, $SO_3H$).

Elemental Analysis: Calcd. for $C_{20}H_{26}FNO_4S$ (m.w. 395.49): C, 60.74%; H, 6.63%; N, 3.54%. Found: C, 60.83%; H, 6.67%; N, 3.54%.

EXAMPLE 16

(2S,3S,5R)-2-(3-fluorophenyl)-3,4,5-trimethylmorpholine hydrochloride m.p. 192°–194° C. $[\alpha]_D^{20}$=+35.4° (c=0.713, 95% ethanol).

NMR-$^1$H: (DMSO-$d_6$) δ 1.07 (d, 3H, $CH_3$), 1.31 (d, 3H, $CH_3$), 2.82 (d, 3H, N-Me); 3.51 (broad m, 2H, CH); 3.79 (dd, 1H, $CH_2$, J=10.94, 12.65), 4.02 (dd, 1H, $CH_2$, J=3.67, 12.55), 4.61 (d, 1H, CH, J=9.96), 7.17–7.51 (aromatic H's), 11.23 (broad, S, 1H, HCl).

Elemental Analysis: Calcd. for $C_{13}H_{19}ClFNO$ (m.w. 259.75): C, 60.11%; H, 7.37%; N, 5.39%. Found: C, 60.06%; H, 7.40%; N, 5.37%.

EXAMPLE 17

(2R,3R,5S)-2-(4-fluorophenyl)-3,4,5-trimethylmorpholine hydrochloride m.p. 193°–194° C. $[\alpha]_D^{20}$=−38.9° (c=0.703, 95% ethanol).

NMR-$^1$H: (DMSO-$d_6$) δ 1.05 (d, 3H, $CH_3$), 1.30 (d, 3H, $CH_3$), 2.83 (d, 3H, N-Me); 3.48 (broad m, 2H, CH), 3.78 (dd, 1H, $CH_2$, J=10.98, 12.70), 4.02 (dd, 1H, $CH_2$, J=3.56, 12.54), 4.58 (d, 1H, CH, J=9.96), 7.17–7.49 (aromatic H's), 11.09 (broad, S, 1H, HCl).

Elemental Analysis: Calcd. for $C_{13}H_{19}ClFNO$ (m.w. 259.75): C, 60.11%; H, 7.37%; N, 5.39%. Found: C, 59.87%; H, 7.42%; N, 5.35%.

EXAMPLE 18

(+−)-(2R*,3R*,5S*)-2-(4-fluorophenyl)-3,4,5-trimethylmorpholine m.p. 72°–74° C.

NMR-$^1$H: ($CDCl_3$) δ 0.84 (d, 3H, $CH_3$), 1.05 (d, 3H, $CH_3$), 2.23 (broad m, 1H, CH); 2.32 (S, 3H, N-Me); 2.44 (broad m, 1H, CH), 3.45 (dd, 1H, $CH_2$, J=10.94, 10.98), 3.81 (dd, 1H, $CH_2$, J=3.32, 11.33); 4.10 (d, 1H, CH, J=9.18), 7.35–7.01 (aromatic H's).

Elemental Analysis: Calcd. for $C_{13}H_{18}FNO$ (m.w. 223.29): C, 69.93%; H, 8.12%; N, 6.27%. Found: C, 69.87%; H, 8.14%; N, 6.25%.

EXAMPLE 19

(2S,3S,5R)-2-(3,4-difluorophenyl)-3,4,5-trimethylmorpholine hydrochloride m.p. 228°–229° C. $[\alpha]_D^{20}=+35.9°$ (c=0.691, 95% ethanol).

NMR-$^1$(DMSO-d$_6$) δ 1.08 (d, 3H, CH$_3$), 1.31 (d, 3H, CH$_3$), 2.81 (d, 3H, N-Me), 3.50 (broad m, 2H, CH), 3.80 (dd, 1H, CH$_2$, J=10.64, 12.53), 4.02 (dd, 1H, CH$_2$, J=3.55, 12.54), 4.65 (d, 1H, CH, J=10.16), 7.23–7.58 (aromatic H's), 11.35 (broad, S, 1H, HCl).

Elemental Analysis: Calcd. for C$_{13}$H$_{18}$ClF$_2$NO (m.w. 277.44): C, 56.22%; H, 6.53%; N, 5.04%. Found: C, 56.22%; H, 6.57%; N, 4.98%.

EXAMPLE 20

(2S,3S,5R)-2-(4-fluorophenyl)-3,4,5-trimethylmorpholine hydrochloride m.p. 193°–194° C. $[\alpha]_D^{20.5}=+38.1°$ (c=0.674, 95% ethanol).

NMR-$^1$H: (DMSO-d$_6$) δ 1.05 (d, 3H, CH$_3$), 1.31 (d, 3H, CH$_3$), 2.82 (d, 3H, N-Me), 3.49 (broad m, 2H, CH), 3.79 (dd, 1H, CH$_2$, J=10.74, 12.65), 4.01 (dd, 1H, CH$_2$, J=3.71, 12.70); 4.60 (d, 1H, CH, J=9.96), 7.17–7.50 (aromatic H's), 11.21 (broad, S, 1H, HCl).

Elemental Analysis: Calcd. for C$_{13}$H$_{19}$ClFNO (m.w. 259.75): C, 60.11%; H, 7.37%; N, 5.39%. Found: C, 60.02%; H, 7.39%; N, 5.38%.

EXAMPLE 21

(2R,3R,5S)-2-(3-fluorophenyl)-3,4,5-trimethylmorpholine hydrochloride m.p. 193°–194° C. $[\alpha]_D^{20}=-35.0°$ (c=0.696, 95% ethanol).

NMR-$^1$H: (DMSO-d$_6$) δ 1.07 (d, 3H, CH$_3$), 1.31 (d, 3H, CH$_3$), 2.82 (d, 3H, N-Me), 3.52 (broad m, 2H, CH), 3.80 (dd, 1H, CH$_2$, J=10.94, 12.50), 4.02 (dd, 1H, CH$_2$, J=3.60, 12.54); 4.62 (d, 1H, CH, J=9.96), 7.17–7.51 (aromatic H's), 11.26 (broad, S, 1H, HCl).

Elemental Analysis: Calcd. for C$_{13}$H$_{19}$ClFNO (m.w. 259.75): C. 60.11%; H, 7.37%; N, 5.39%. Found: C. 60.22%; H, 7.39%; N, 5.41%.

EXAMPLE 22

Antitetrabenazine Test

Prevention of tetrabenazine-induced sedation was measured using a modification of the method of Vernier et al., *First Hahnemann Symposium on Psychosomatic Medicine*, ed. Nodim and Moyer, pub. Lea and Febiger, Philadelphia, 1962.

Mice, groups of 12 CD1 males each, were injected intraperitoneally (ip) with the hydrochloride salt of a compound of formula (I) in physiological saline solution or with physiological saline solution alone. Thirty minutes later each of the mice was injected (ip, 35 mg/kg) with a solution of tetrabenazine hydrochloride. Thirty minutes after the injection of tetrabenazine each mouse was examined for its level of exploratory behavior which was scored on a modification of the arbitrary scale defined by Vernier et. al. The result reported in Table I as the ED$_{50}$ value is the amount of the test compound required to reverse the tetrabenazine effects in 50 percent of the animals tested.

TABLE I

Antitetrabenazine Activity in the Mouse

| Compound | ED$_{50}$ (mg/kg i.p.) |
|---|---|
| Example 1 (HCl) | 4 |
| Example 2 (HCl) | 8 |
| Example 6 (HCl) | 10 |
| Example 7 (HCl) | 4 |
| Example 12 (HCl) | 6 |
| Example 13 (HCl) | 4 |
| Example 14 (HCl) | 8 |
| Example 16 (HCl) | 8 |
| Example 18 | 6 |

EXAMPLE 23

Formulations

A. Tablet

| Ingredient | Amount per Tablet |
|---|---|
| A compound of formula (I) (calculated as the base) | 50 mg |
| Lactose | 85 mg |
| Cornstarch | 50 mg |
| Micronized Silica Gel | 10 mg |
| Polyvinylpyrrolidone | 5 mg |

The lactose, cornstarch and compound of formula (I) are mixed together and granulated with a binder (polyvinylpyrrolidone in an alcoholic solution) to form granules. The granules are passed through a 16–20 mesh screen, then air dried, lubricated with micronized silica gel and compressed into tablets. A film coat may then be applied if desired.

B. Capsule

| Ingredient | Amount per Capsule |
|---|---|
| A compound of formula (I) (calculated as the base) | 50 mg |
| Lactose | 125 mg |
| Cornstarch | 125 mg |

The above ingredients are mixed and filled into a two piece hard gelatin capsule.

C. Parenteral Solution

| A compound of formula (I) as a parmaceutically acceptable salt) | 25 mg (calculated as the base) |
|---|---|
| Sterile Water for Injections, q.s. to | 1.0 ml |

A pharmaceutically acceptable salt of a compound of formula (I) is dissolved in sterile water under sterile conditions to make 1.0 mL. Such a solution may be packaged in a sealed sterile ampule to provide a unit dose or in a sterile vial for multiple doses. If the formulation is to be packed in a multi-dose container, the addition of a bacteriostat such as 0.2 to 0.5% w/v of phenol is desirable.

D. Suppository

The hydrochloride salt of a compound of formula (I) (50 mg, calculated as the base) is mixed with 250 mg of softened or melted cocoa butter, and a suppository is formed by chilling and shading in a mold.

We claim:

1. A method for the treatment of depression in a human being, the method comprising administering to the human being an antidepressant effective amount of a compound of the following formula

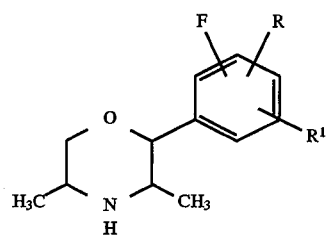

or a pharmaceutically acceptable salt thereof, wherein R and $R^1$ are independently hydrogen or fluorine.

2. The method for treatment of depression in accord with claim 1, wherein the compound is 2-(3-fluorophenyl)-3,5-dimethylmorpholine.

3. The method for treatment of depression in accord with claim 1, wherein the compound is 2-(3,4-difluorophenyl)-3,5-dimethylmorpholine.

4. The method for treatment of depression in accord with claims 1, 2 or 3, wherein the compound or its salt is administered orally.

5. The method for treatment of depression in accord with claims 1, 2 or 3, wherein the compound or its salt is administered with a pharmaceutically acceptable carrier.

6. The method for treatment of depression in accord with claims 5, wherein the compound or its salt is administered orally.

7. The method for treatment of depression in accord with claim 4, wherein the compound or its salt is administered in the form of an orally ingestible capsule or tablet.

8. The method for treatment of depression in accord with claim 6, wherein the compound or its salt is administered in the form of an orally ingestible capsule or tablet.

* * * * *